United States Patent [19]

Katagiri et al.

[11] Patent Number: 4,487,824
[45] Date of Patent: Dec. 11, 1984

[54] ELECTROPHOTOGRAPHIC PHOTOSENSITIVE MEMBER CONTAINING A HALOGEN SUBSTITUTED HYDRAZONE

[75] Inventors: Kazuharu Katagiri, Yokohama; Katsunori Watanabe, Toride; Kiyoshi Sakai, Mitaka; Shozo Ishikawa; Makoto Kitahara, both of Yokohama, all of Japan

[73] Assignee: Canon Kabushiki Kaisha, Tokyo, Japan

[21] Appl. No.: 492,632

[22] Filed: May 9, 1983

[51] Int. Cl.³ .............................................. G03G 5/06
[52] U.S. Cl. ..................................... 430/58; 430/73; 430/74
[58] Field of Search .................. 430/70, 75, 73, 74, 430/71, 79, 58

[56] References Cited

U.S. PATENT DOCUMENTS

| | | |
|---|---|---|
| 3,180,729 | 4/1965 | Klupfel et al. . |
| 3,378,554 | 4/1968 | Pushchel et al. . |
| 3,484,237 | 12/1969 | Shattuck et al. . |
| 3,684,502 | 8/1972 | Gramza et al. . |
| 3,775,105 | 11/1973 | Kukla . |
| 3,775,108 | 11/1973 | Fliari . |
| 3,824,099 | 7/1974 | Champ et al. . |
| 3,837,851 | 9/1974 | Shattuck et al. . |
| 3,870,516 | 3/1975 | Smith et al. . |
| 3,871,882 | 3/1975 | Wiedemann . |
| 3,877,935 | 4/1975 | Regensburger et al. . |
| 3,884,691 | 5/1975 | Rochlitz . |
| 3,894,868 | 7/1975 | Regensburger et al. . |
| 4,024,125 | 5/1977 | Kunstmann et al. . |
| 4,122,113 | 10/1978 | Purner . |
| 4,150,987 | 4/1979 | Anderson et al. . |
| 4,251,614 | 2/1981 | Sasaki et al. . |
| 4,256,821 | 3/1981 | Enomoto et al. . |
| 4,260,672 | 4/1981 | Sasaki . |
| 4,265,991 | 5/1981 | Hirai et al. . |
| 4,272,598 | 6/1981 | Sasaki et al. . |
| 4,278,747 | 7/1981 | Murayama ............... 430/70 |
| 4,279,981 | 7/1981 | Ohta et al. . |
| 4,297,426 | 10/1981 | Sakai et al. . |

FOREIGN PATENT DOCUMENTS

| | | |
|---|---|---|
| 0013172 | 7/1980 | European Pat. Off. . |
| 2302522 | 8/1974 | Fed. Rep. of Germany . |
| 43-1619768 | 7/1968 | Japan . |
| 48-7123673 | 9/1973 | Japan . |
| 54-112637 | 9/1979 | Japan . |
| 54-119925 | 9/1979 | Japan . |
| 54-121742 | 9/1979 | Japan . |
| 55-108667 | 8/1980 | Japan . |
| 930988 | 7/1963 | United Kingdom . |
| 1030024 | 5/1966 | United Kingdom . |
| 1296390 | 11/1972 | United Kingdom . |
| 1370197 | 10/1976 | United Kingdom . |
| 1453024 | 10/1976 | United Kingdom . |
| 1465141 | 2/1977 | United Kingdom . |
| 1465142 | 2/1977 | United Kingdom . |
| 1490197 | 10/1977 | United Kingdom . |
| 2001769A | 2/1979 | United Kingdom . |
| 2018446A | 10/1979 | United Kingdom . |
| 2034493A | 6/1980 | United Kingdom . |
| 2052082A | 1/1981 | United Kingdom . |
| 2055803A | 3/1981 | United Kingdom . |
| 2034494A | 6/1982 | United Kingdom . |

Primary Examiner—John E. Kittle
Assistant Examiner—John L. Goodrow
Attorney, Agent, or Firm—Fitzpatrick, Cella, Harper & Scinto

[57] ABSTRACT

An electrophotographic photosensitive member comprises an electrically conductive substrate and a layer containing a hydrazone compound represented by the following formula (1) and a binder:

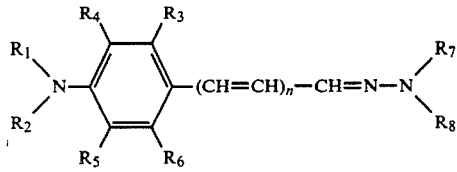

wherein; $R_1$ and $R_2$ each represent alkyl, aralkyl, or aryl, substituted or unsubstituted, or $R_1$ and $R_2$ together with the nitrogen atom to which they are attached form a 5- or 6-membered ring; $R_3$ represents halogen or fluoroalkyl; $R_4$ and $R_6$ each represent hydrogen or halogen; $R_5$ represents hydrogen, alkyl, alkoxyl, or halogen; each of $R_7$ and $R_8$ represents alkyl, aralkyl, or aryl, substituted or unsubstituted; and n represents an integer of 0 or 1.

25 Claims, No Drawings

ELECTROPHOTOGRAPHIC PHOTOSENSITIVE MEMBER CONTAINING A HALOGEN SUBSTITUTED HYDRAZONE

BACKGROUND OF THE INVENTION

1. Field of the Invention

This invention relates to electrophotographic photosensitive members and more particularly to an electrophotographic photosensitive member comprising an organic photoconductive material which can provide improved electrophotographic characteristics to the member.

2. Description of the Prior Art

Inorganic photoconductive materials such as selenium, cadmium sulfide, zinc oxide, etc. have so far been known as those for use in electrophotographic photosensitive members. While having many advantages, for example, chargeability in the dark to a suitable potential, little dissipation of charge in the dark, and fast dissipation possible on light irradiation, these photoconductive materials have various disadvantages. For example, a drawback of selenium type photosensitive members is that the crystallization of photoconductive materials readily proceeds by the action of factors such as temperature, humidity, dust, pressure, and the like, which becomes remarkable when the atmospheric temperature exceeds 40° C., resulting in decreased chargeability and white spots on the developed images. Cadmium sulfide type photosensitive members have a drawback in that they cannot maintain stable photosensitivity under high humidity environmental conditions. While zinc oxide type photosensitive members need sensitization with a sensitizing colorant, a typical example of which is Rose Bengal, a drawback of these photosensitive members is that stable formations of images for a long period of time are impossible because such a colorant promotes the deterioration of chargeability by corona charging and undergoes fading upon light exposure.

On the other hand, various organic photoconductive polymers have been proposed including polyvinylcarbazole. Although superior to the above inorganic photoconductive materials in film-forming property and lightness, these polymers have been rarely put to practical use until now, since the film-forming property thereof is not yet sufficient and they are inferior to inorganic photoconductors in sensitivity, durability, and stability to changes of environmental conditions. Low molecular weight organic photoconductive materials also have been proposed, including hydrazone compounds as disclosed in U.S. Pat. No. 4,150,987, triarylpyrazoline compounds as disclosed in U.S. Pat. No. 3,837,851, and 9-styrylanthracene derivatives as disclosed in Japanese Pat. Kokai Nos. 94828/1976 and 94829/1976. These organic photoconductive materials have overcome the drawback of insufficient film-forming property, which has been a problem in the field of organic photoconductive polymers, by incorporating therein a suitable binder. However, they lack sufficient sensitivity.

In view of the above, photosensitive members of laminate structure have been recently proposed wherein the photosensitive layer has been divided into two layers functioning separately as a charge generation layer and a charge transport layer. The electrophotographic photosensitive member having such photosensitive layers of laminate structure is improved in sensitivity to visible light, electric charge retention, and surface strength. These photosensitive members have been disclosed in U.S. Pat. Nos. 3,837,851 and 3,871,882.

Nevertheless, electrophotographic photosensitive members employing conventional organic photoconductive materials have deficiencies to be corrected, since their sensitivity is still insufficient and variations in light portion potential and dark portion potential are significant when they are charged and exposed repeatedly.

SUMMARY OF THE INVENTION

An object of this invention is to provide an electrophotographic photosensitive member overcoming the above noted drawbacks or disadvantages.

Another object of this invention is to provide a novel organic photoconductive material.

A further object of this invention is to provide a novel charge-transporting material for use in photosensitive members comprising two laminated photosensitive layers functioning separately as a charge generation layer and a charge transport layer.

These objects can be achieved with an electrophotographic photosensitive member comprising a layer comprising a hydrazone compound represented by the formula

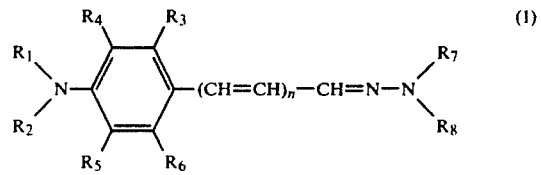

(1)

wherein; $R_1$ and $R_2$ each represent alkyl, aralkyl, or aryl, substituted or unsubstituted, or $R_1$ and $R_2$ together with the nitrogen atom to which they are attached form a 5- or 6-membered ring; $R_3$ represents halogen or fluoroalkyl; $R_4$ and $R_6$ each represent hydrogen or halogen; $R_5$ represents hydrogen, alkyl, alkoxyl, or halogen; $R_7$ and $R_8$ each represent alkyl, aralkyl, or aryl, substituted or unsubstituted; and n represents an integer of 0 or 1.

DETAILED DESCRIPTION OF THE INVENTION

The electrophotographic photosensitive member of this invention has a layer containing a hydrazone compound represented by the following formula (1) and a binder:

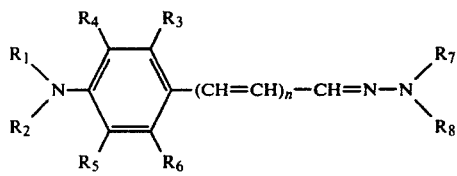

In the formula (1); $R_1$ and $R_2$ each represent alkyl such as methyl, ethyl, propyl, or butyl; aralkyl such as benzyl, phenethyl, or naphthylmethyl; or aryl such as phenyl; any of these groups being unsubstituted or substituted by alkyl (e.g. methyl, ethyl, propyl, or butyl), alkoxyl (e.g. methoxy, ethoxy, propoxy, or butoxy), halogen (e.g. fluorine, chlorine, bromine, or iodine), or dialkylamino (e.g. dimethylamino, diethylamino, dipropylamino, or dibutylamino; alternatively, $R_1$ and $R_2$ together with the nitrogen atom to which they are attached may form a 5- or 6-membered ring such as pyrrolidinyl, piperidino, or morpholino.

$R_3$ represents halogen such as fluorine, chlorine, bromine, or iodine; or fluoroalkyl such as trifluoromethyl, fluroethyl, fluoropropyl, or fluorobutyl. $R_4$ and $R_6$ each represent hydrogen or halogen such as fluorine, chlorine, bromine, or iodine. $R_5$ represents hydrogen; alkyl such as methyl, ethyl, propyl, or butyl; alkoxyl such as methoxy, ethoxy, propoxy, or butoxy; or halogen such as fluorine, chlorine, bromine, or iodine.

Each of $R_7$ and $R_8$ represents alkyl such as methyl, ethyl, propyl, or butyl; aralkyl such as benzyl, phenethyl, or naphthylmethyl; or aryl such as phenyl, naphthyl or anthryl; any of these groups can have the same substituent as cited above referring to $R_1$ and $R_2$. The small letter n is an integer of 0 or 1.

The hydrazone compound of this invention has a structural characteristic in that $R_5$ in the formula (1) is halogen or fluoroalkyl, whereby the electrophotographic photosensitive member of this invention exhibits excellent electrophotographic sensitivity and long-term potential stability.

Typical hydrazone compounds of the formula (1) used in this invention are listed below.

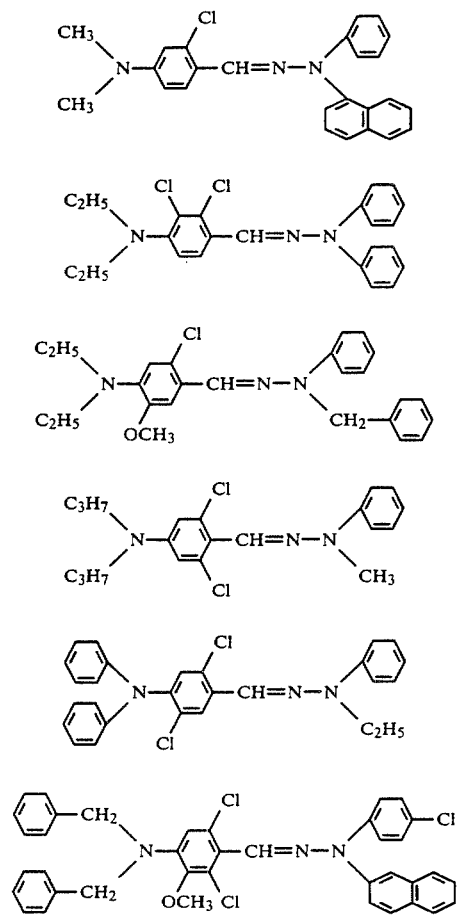

-continued

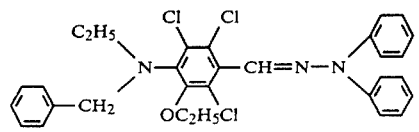
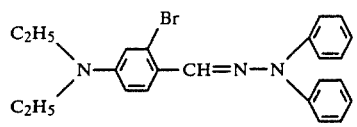
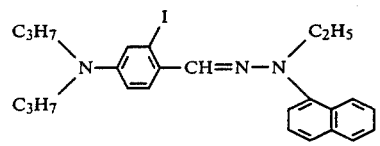
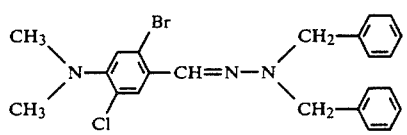
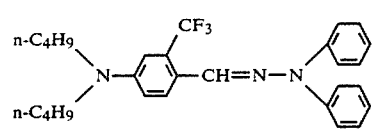
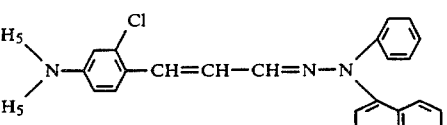
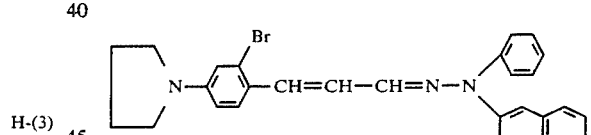
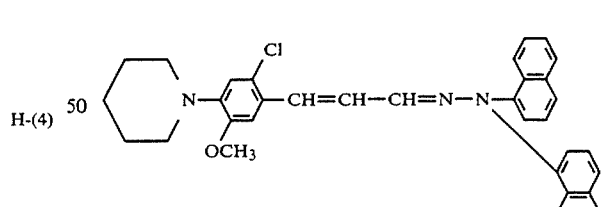
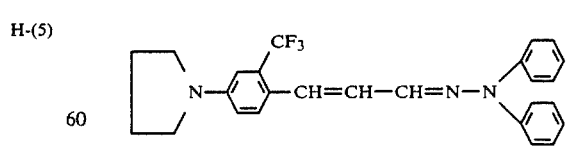
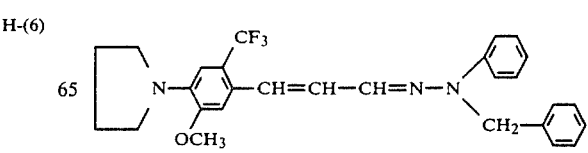

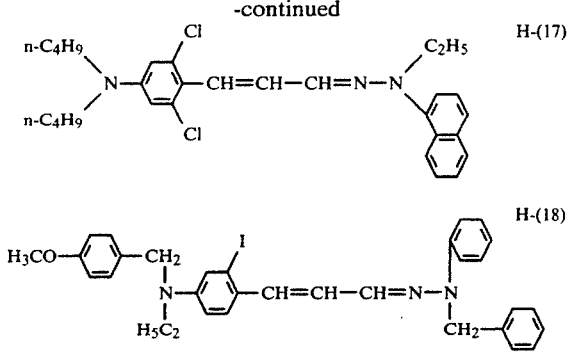

These compounds can be synthesized by treating first a solution of a secondary amine in a glacial acetic acid-ethanol (1:1) mixture with sodium nitrite to form the corresponding nitroso compound, reducing this with zinc dust to give a solution of the corresponding hydrazine compound, filtering off precipitated matter, adding a benzaldehyde derivative dissolved in ethanol to the filtrate, and subjecting the mixture to condensation reaction at room temperature.

A preparation example is given below referring to Compound H-(1) listed above.

Phenyl-α-naphthylamine (7.7 g, 0.035 mole) was dispersed in a mixture of 40 ml of ethanol and 40 ml of glacial acetic acid. Sodium nitrite (2.7 g 0.039 mole) was added to the dispersion with stirring at room temperature during 10 minutes, and the stirring was continued for one further hour. Zinc dust (10.0 g, 0.15 mole) was added during 10 minutes while keeping the liquid temperature at 20°–35° C. with an ice bath. The mixture was further stirred for 40 minutes, the resulting precipitate was filtered off, and a solution of α-chloro-4-dimethylaminobenzaldehyde (5.2 g, 0.028 mole) in 30 ml of ethanol was added to the filtrate with stirring at room temperature. After further stirring for 2 hours, the resulting crystals were filtered off, and recrystallized from a methanol-methyl ethyl ketone mixture. Thus, 5.2 g of the objective hydrazone compound H-(1) was obtained in a pale yellow crystalline form, yield 46.4%, m.p. 140.0°–141.0° C.

Anal. (%), Calcd. for $C_{25}H_{22}N_3Cl$: C75.08, H5.55, N10.51, Cl 8.86; Found: C75.03, H5.47, N10.46, Cl 8.76.

In preferred embodiments of this invention, the hydrazone compound of the formula (1) is used as a charge-transporting material for electrophotographic photosensitive members provided with two photosensitive layers functioning separately as a charge generation layer and a charge transport layer.

The charge transport layer according to this invention is preferably formed by applying the hydrazone compound of the formula (1) dissolved together with a binder in a suitable solvent and drying it. Binders used herein include, for example, polyarylates, polysulfone, polyamides, acrylic resins, polyacrylonitrile, methacrylic resin, vinyl chloride resin, vinyl acetate resin, phenolic resins, epoxy resins, polyesters, alkyd resins, polycarbonates, polyurethanes, and copolymers such as styrene-butadiene copolymer, styreneacrylonitrile copolymer, and styrene-maleic acid copolymer. Besides these insulating polymers, organic photoconductive polymers can be used such as polyvinylcarbazole, polyvinylanthracene, polyvinylpyrene, and the like.

Suitable compouding ratios of the binder to the hydrazone compound are 100:10–100:500 by weight.

The charge transport layer communicates electrically with the charge generation layer, which will be described later, and has the functions to receive charge carriers injected from the charge generation layer in an electric field and to transport these charge carriers to its surface. The charge transport layer may be laminated on either the upper side or the lower side of the charge generation layer but preferably on the upper side. The thickness of the charge transport layer cannot be enlarged more than is necessary, since the range of transporting charge carriers is limited. The thickness is generally in the range 5–30μ, preferably 8–20μ.

The organic solvent used for the coating to form the charge transport layer varies depending upon the kind of the binder used and is desirably selected from those which do not dissolve the charge generation layer or an under coating layer which will be described later. Examples of the solvent usable are alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethylsulfoxide; ethers such as tetrahydrofuran, dioxane, and ethylene glycol monomethyl ether; esters such as methyl acetate and ethyl acetate; halogenated aliphatic hydrocarbons such as chloroform, methylene chloride, dichloroethylene, carbon tetrachloride, and trichloroethylene; and aromatic solvents such as benzene, toluene, xylene, ligroin, monochlorobenzene, and dichlorobenzene.

The coating for forming the charge transport layer can be accomplished by the dip coating, spray coating, spinner coating, bead coating, Meyer bar coating, blade coating, roller coating, curtain coating, etc. Desirably, the coating, after set to touch at room temperature, is dried by heating at 30°–200° C. for 5 minutes—2 hours with or without blowing air.

Various additives can be incorporated in the charge transport layer of this invention. Such additives include, for example, diphenyl, o-terphenyl, o-terphenyl, dibutyl phthalate, dimethyl glycol phthalate, dioctyl phthalate, triphenyl phosphate, methylnaphthalene, benzophenone, chlorinated paraffin, dilauryl thiodipropionate, 3,5-dinitrosalicylic acid, and various fluorocarbons.

A suitable charge generation layer of this invention is a vapor deposition layer of a charge-generating material or a layer of its dispersion in a binder. The charge generating material is selected from selenium, selenium-tellurium, pyrylium dyes, thiopyrylium dyes, phthalocyanine pigments, anthoanthrone pigments, dibenzypyrenequinone pigments, pyranethrone pigments, trisazo pigments, disazo pigments, monoazo pigments, indigo dyes, quinacridone pigments, asymmetric quinocyanine dyes, quinocyanine dyes, and amorphous silicon, which is described in Japanese Pat. Kokai No. 143645/1979. Various examples of the inorganic or organic charge-generating materials are listed below.

| | |
|---|---|
| Amorphous silicon | (1) |
| Selenium-tellurium | (2) |
| Selenium-arsenic | (3) |
| Cadmium sulfide | (4) |

-continued
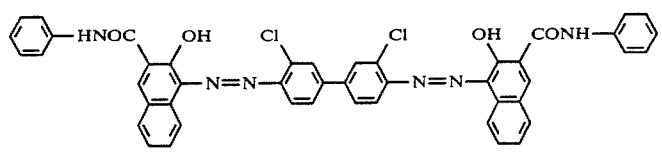
(5)
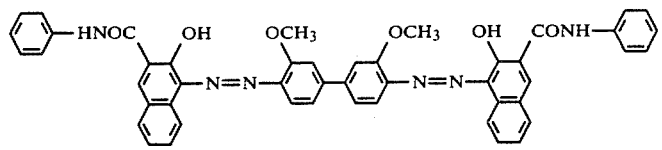
(6)
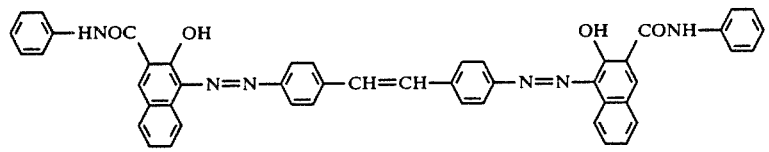
(7)
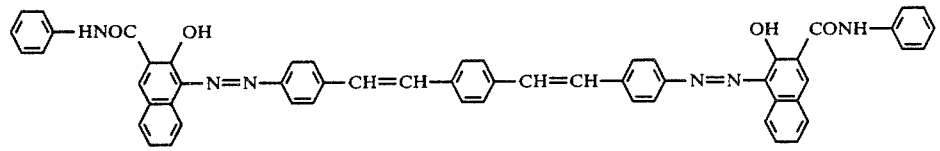
(8)
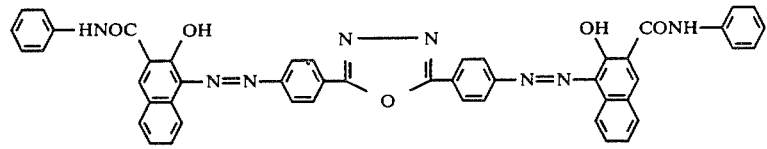
(9)
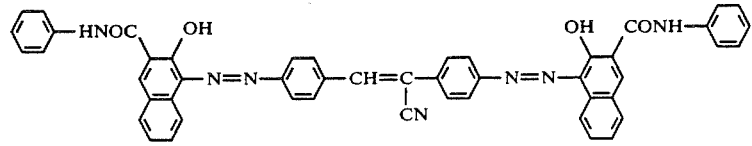
(10)
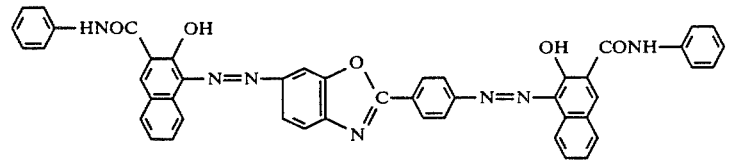
(11)
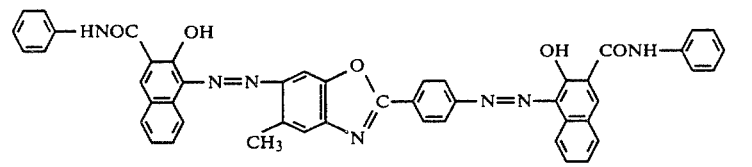
(12)
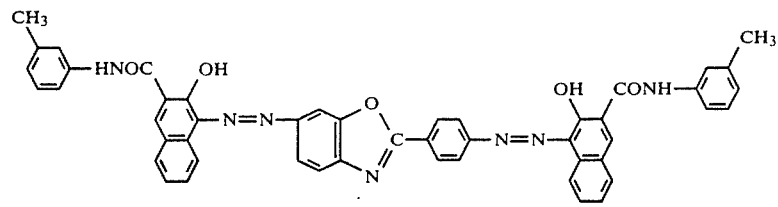
(13)

-continued
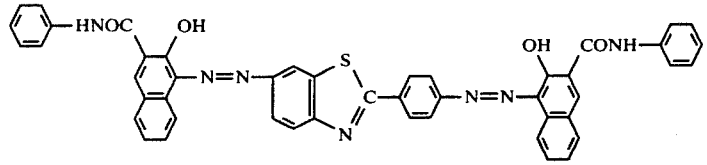 (14)
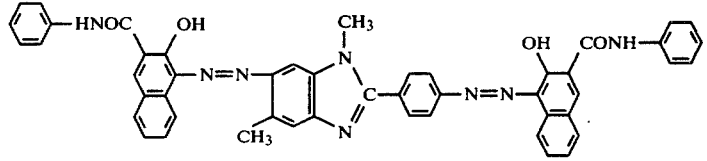 (15)
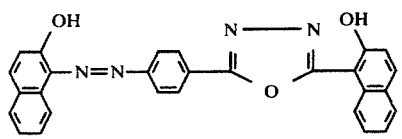 (16)
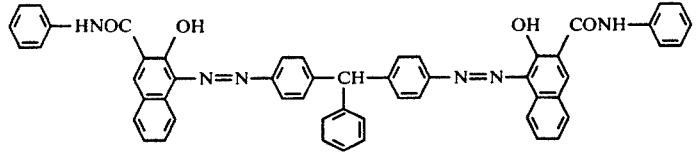 (17)
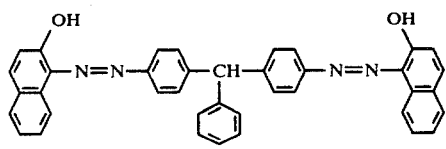 (18)
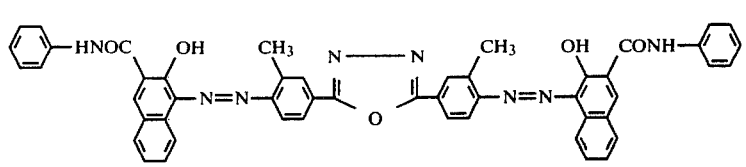 (19)
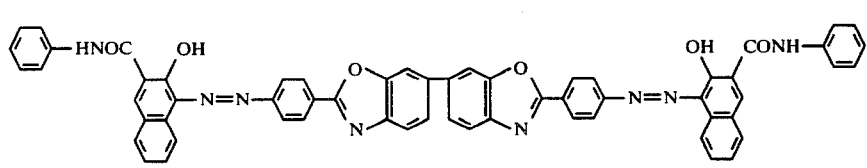 (20)
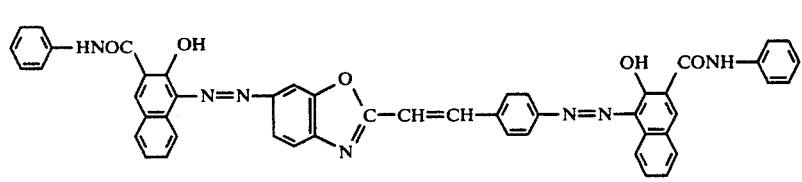 (21)
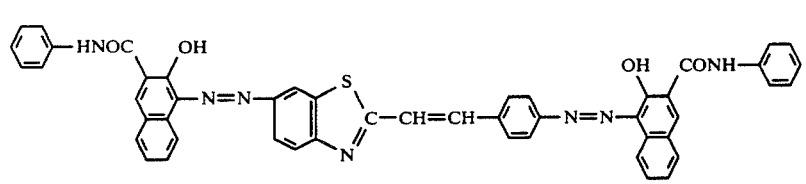 (22)

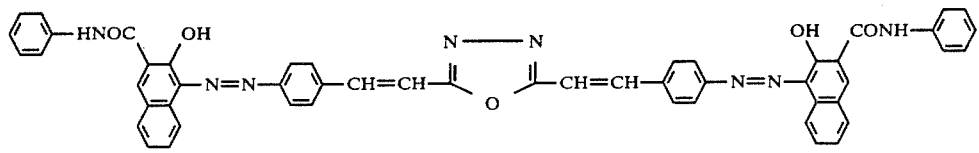 (23)
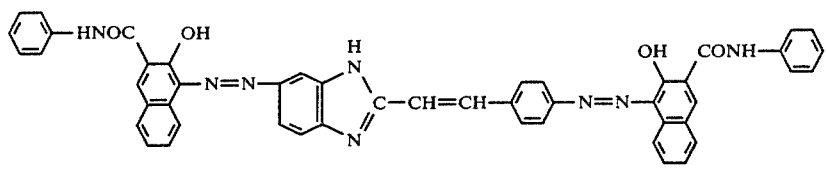 (24)
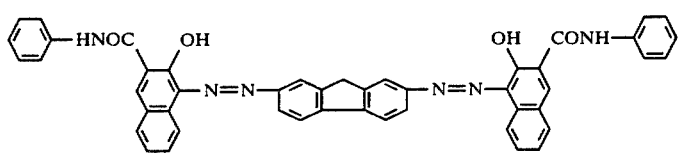 (25)
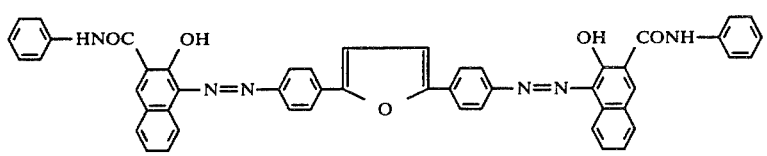 (26)
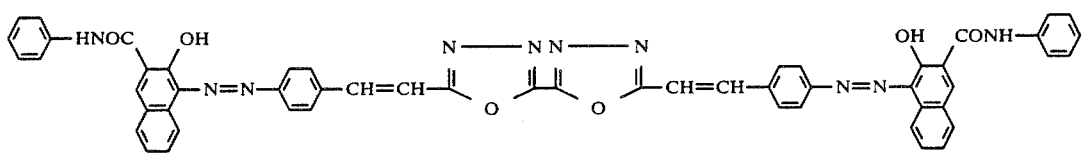 (27)
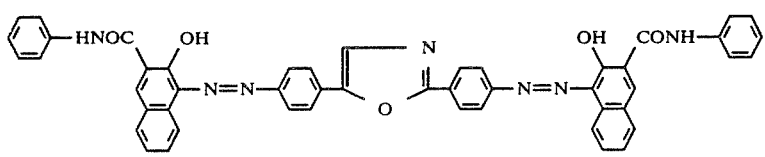 (28)
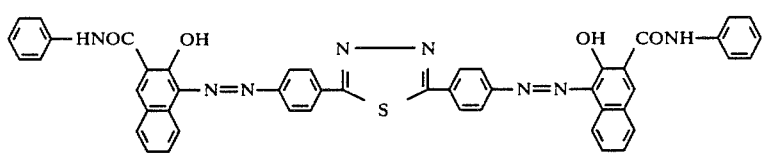 (29)
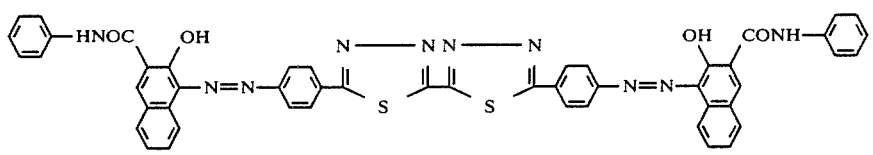 (30)
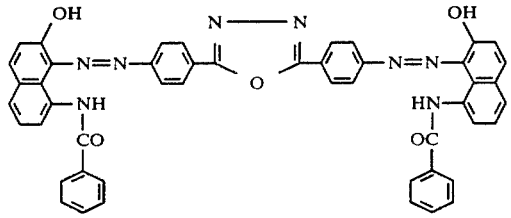 (31)
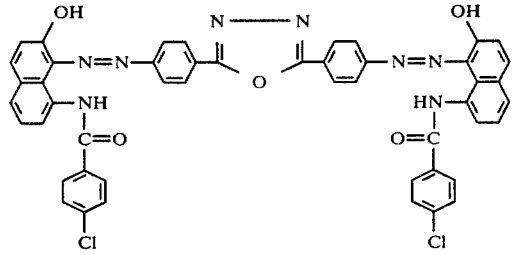 (32)

-continued
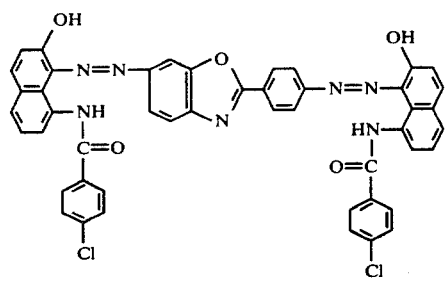 (33)
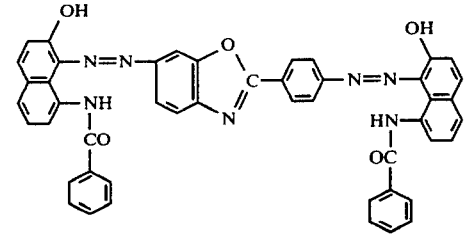 (34)
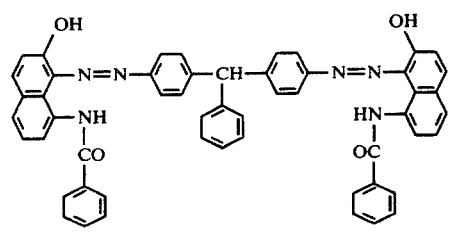 (35)
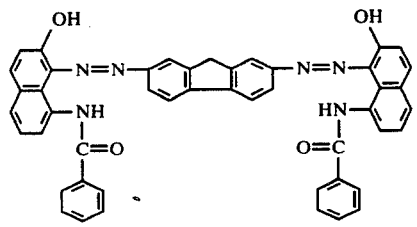 (36)
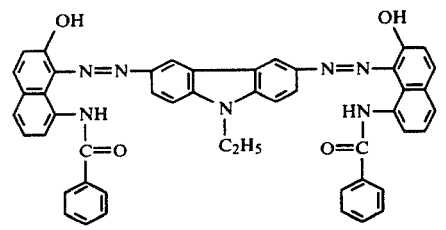 (37)
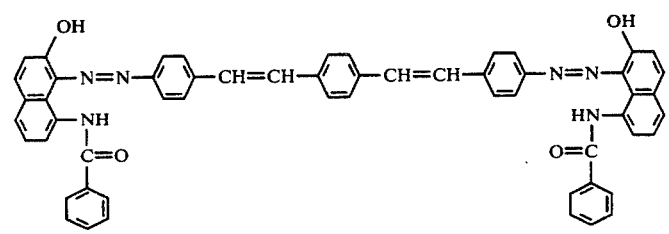 (38)
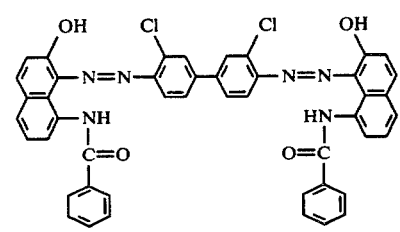 (39)
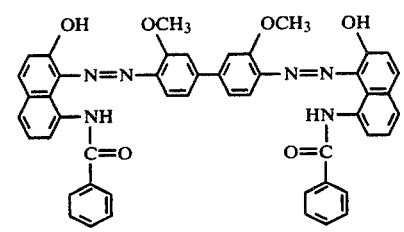 (40)
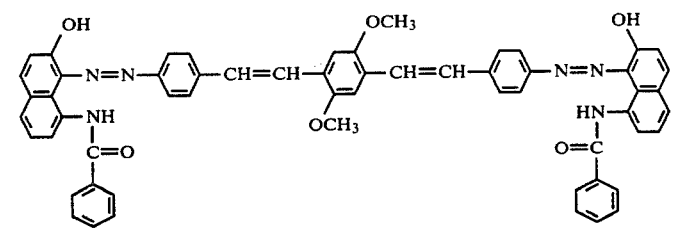 (41)

-continued
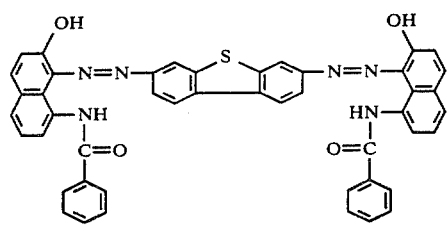 (42)
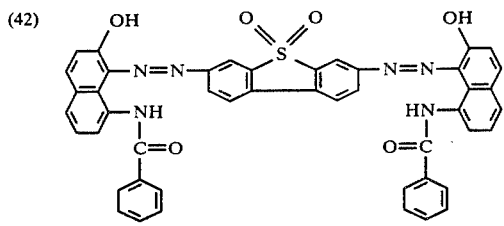 (43)
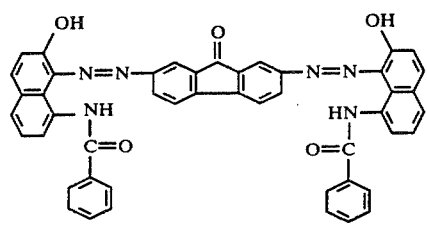 (44)
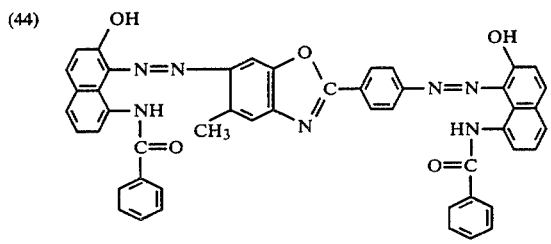 (45)
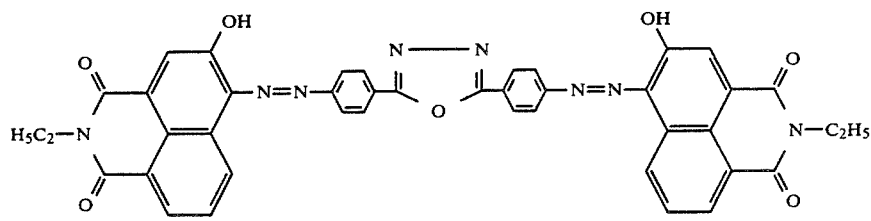 (46)
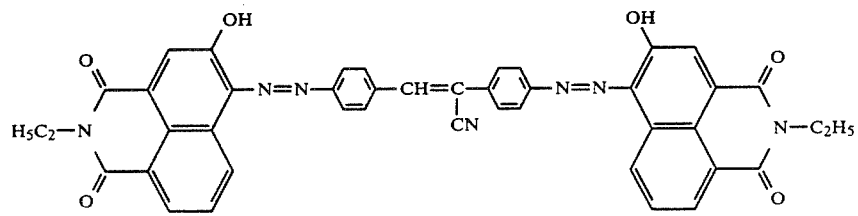 (47)
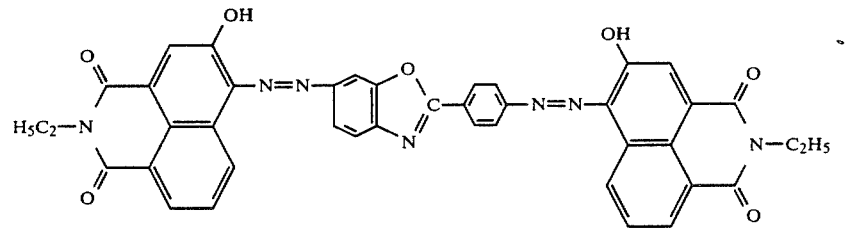 (48)
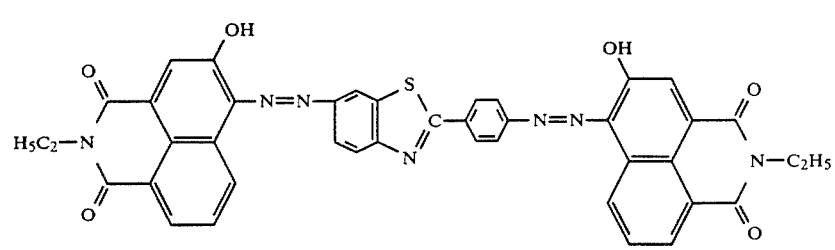 (49)

-continued
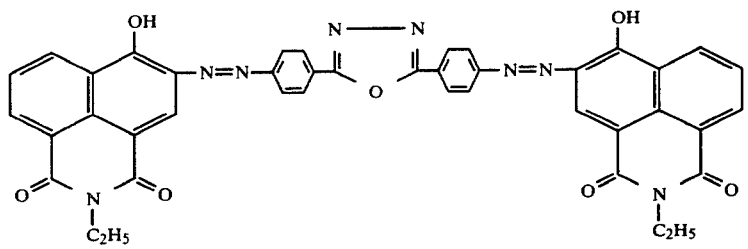 (50)
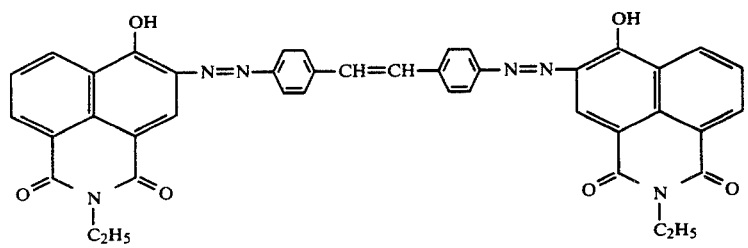 (51)
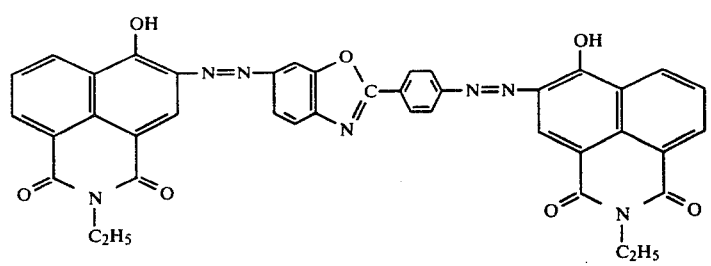 (52)
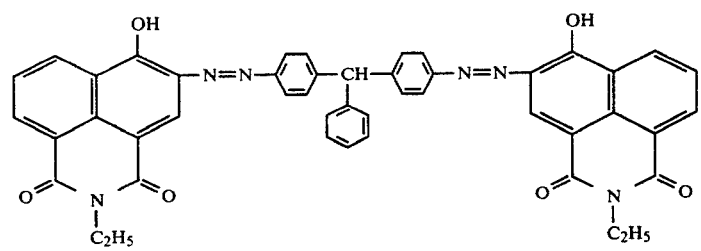 (53)
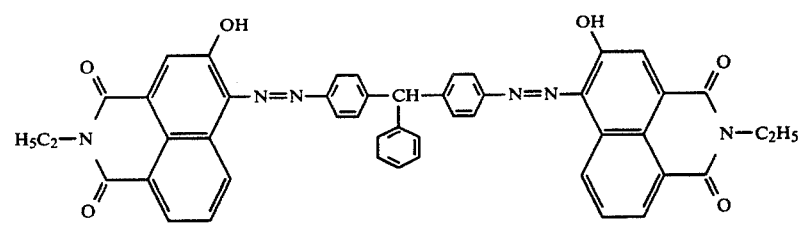 (54)
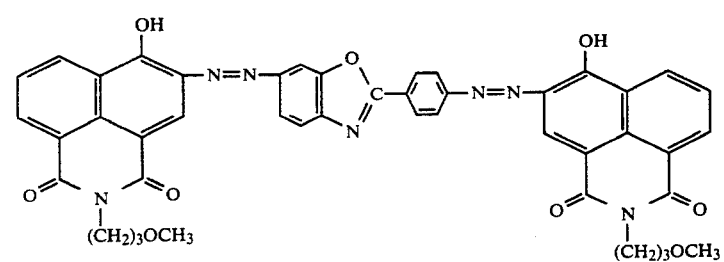 (55)

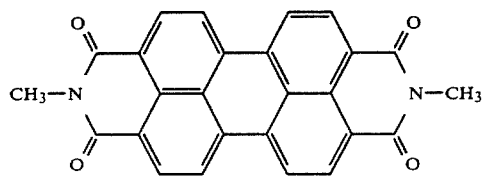 (56)

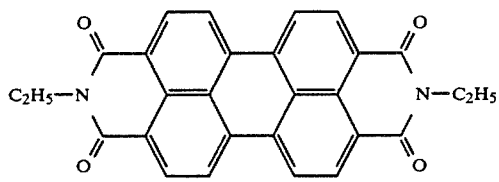 (57)

Squaric acid dyes (58)
Indigo dyes (C.I. No. 78,800) (59)
Thiodio dyes (C.I. No. 78,800) (60)
β-type of copper phthalocyanine (61)

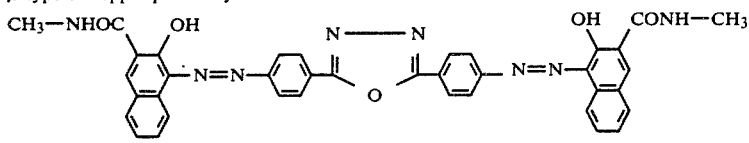 (62)

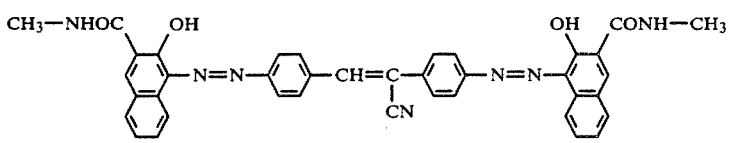 (63)

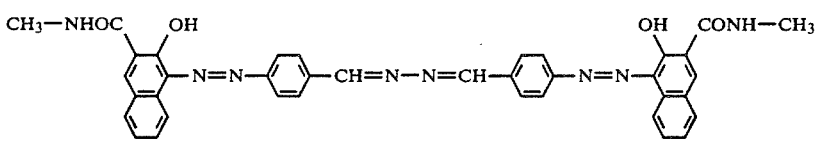 (64)

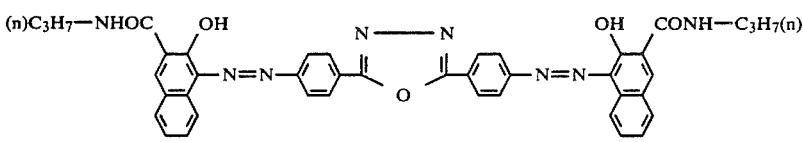 (65)

The charge generation layer can be formed on a substrate by coating it with a dispersion, in a suitable binder, of a charge-generating material selected from the above-listed photoconductive pigments and dyes or by vapor deposition of a charge-generating material selected from the above-listed inorganic or organic photoconductive materials.

The binder used for the formation of the charge generation layer by coating can be selected from a wide variety of insulating resins and from organic photoconductive polymers such as poly(N-vinylcarbazole), polyvinylanthracene, and polyvinylpyrene. The following insulating resins can be given as preferred examples of the binder: poly(vinyl butyral), polyacrylates(e.g. a condensation polymer of bisphenol A and phthalic acid), polycarbonates, polyesters, phenoxy resins, poly(vinyl acetate), acrylic resin, polyacrylamides, polyamides, polyvinylpyridine, cellulosic resins, urethane resins, epoxy resins, casein, poly(vinyl alcohol), and polyvinylpyrrolidone. Suitable contents of the binder resin in the charge generation layer are up to 80%, preferably up to 40%, by weight.

Organic solvents usable for the coating include, for example, alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethylsulfoxide; ethers such as tetrahydrofuran, dioxane, and ethylene glycol monomethyl ether; esters such as methyl acetate and ethyl acetate; halogenated aliphatic hydrocarbons such as chloroform, methylene chloride, dichloroethylene, carbon tetrachloride, and trichloroethylene; and aromatic solvents such as benzene, toluene, xylene, ligroin, monochlorobenzene, and dichlorobenzene.

The coating for forming the charge generation layer can be accomplished by the dip coating, spray coating, spinner coating, bead coating, Meyer bar coating, blade coating, roller coating, curtain coating etc.

The charge generation layer is desired to contain as much of the abovementioned organic photoconductor as possible for the purpose of attaining a light absorption sufficient to generate a great number of charge carriers. In addition, this layer is desired to be no thicker than 5μ, preferably 0.01–1μ for the purpose of effective injection of the generated charge carriers to the charge transport layer. This is necessary since the majority of incident light is absorbed into the charge generation layer to generate a great number of charge carriers and that the generated charge carriers are injected into the charge transport layer without deactivation by recombination or trapping. It is also possible to form the charge generation layer from the photoconductive dye or pigment by the above-mentioned coating method without using any binder.

These laminated photosensitive layers of charge generation and charge transport are formed on an electrically conductive substrate. Materials for use as the conductive substrate include films or sheets of metals and alloys, which have conductivity in themselves, for example, aluminum, aluminum alloys, copper, zinc, stainless steel, vanadium, molybdenum, chromium, titanium, nickel, indium, gold, and platinum; films or sheets of plastics [e.g. polyethylene, polypropylene, poly(vinyl chrolide), poly(ethylene terephthalate), acrylic resin, and polyfluoroethylene] which are overlaid with a vacuum deposition film of aluminum, aluminum alloy, indium oxide, tin oxide, or indium oxide—tin oxide alloy or with a mixture of conductive particles (e.g. carbon black or silver particles) and a suitable binder; and films or sheets of similar plastics and paper which are impregnated with conductive particles (the above particles or conductive polymer particles), and of plastics comprising a conductive polymer.

An under coating layer having both barrier function and bonding function can be laid as an intermediary layer between the conductive layer and the photosensitive layer. The undercoating layer can be formed from casein, poly(vinyl alcohol), nitrocellulose, ethylene-acrylic acid copolymer, polyamides(e.g. nylon 6, nylon 66, nylon 610, nylon copolymer, or alkoxymethylated nylon), polyurethanes, gelatin, aluminum oxide, or the like. Thickness of the under coating layer is desirably 0.1–5μ, preferably 0.5–3μ.

The photosensitive member, according to this invention, having a charge generation layer and charge transport layer laminated in this order on a conductive substrate can be operated by placing negative electric charge on the charge transport layer, because the hydrazone compound is a hole-transporting material, and exposing the photosensitive layers to a pattern of light. Thus, in the exposed areas, holes produced in the charge generation layer are injected into the charge transport layer, then arrive at the surface, and neutralize the negative charge, thereby decaying the surface potential and producing an electrostatic contrast to the unexposed areas. The development can be carried out by using a positively charged toner. When using an electron-transporting material, a negatively charged toner can be used. This invention can also be applied to a photosensitive member having a charge transport layer and charge generation layer laminated in this order on a conductive substrate.

In another embodiment of this invention, a photoconductive pigment or dye can be used as a sensitizer. Such pigments and dyes are, for example, the above listed disazo pigments and the dyes disclosed in U.S. Pat. Nos. 3,554,745, 3,567,438, and 3,586,500, such as pyrylium dye, thiopyrylium dye, selenopyrylium dye, benzopyrylium dye, benzothiopyrylium dye, naphtholpyrylium dye, and naphthothiopyrylium dye.

In a further embodiment of this invention, a photoconductive co-crystalline complex of a pyrylium dye and an electrically insulating polymer having alkylidenediarylene segments can be used as a sensitizer, which has been disclosed in U.S. Pat. No. 3,684,502. For example, this co-crystalline complex can be obtained in granular form by adding a nonpolar solvent (e.g. hexane, octane, decane, trimethylbenzene, or ligroin) to a solution of 4-[4-bis(2-chloroethyl) aminophenyl]-2,6-diphenylthiopyrylium perchlorate and poly(4,4'-isopropylidenediphenylene carbonate) in a halogenated hydrocarbon solvent(e.g. dichloromethane, chloroform, carbon tetrachloride, 1,1-dichloroethane, 1,2-dichloroethane, 1,1,2-trichloroethane, chlorobenzene, bromobenzene, or 1,2-dichlorobenzene). In this embodiment, a polymer selected from the following can be used as a binder: styrene-butadiene copolymer, silicone resins, vinyl chloride resin, vinyl acetate resin, styrene resin, vinylidene chloride-acrylonitrile copolymer, styrenescrylonitrile copolymer, vinyl acetate-vinyl chloride copolymer, poly(vinyl butyral), poly(methyl methacrylate), poly(n-butyl methacrylate), polyesters, cellulose ester, etc.

The electrophotographic photosensitive member of this invention can be used not only in electrophotographic copying machines but also over a wide field of electrophotographic applications such as those to laser printers, CRT printers, and electrophotographic printingplate making systems.

According to this invention, it is possible to provide high sensitivity electrophotographic photosensitive members which exhibit little variations in light portion potential and dark portion potential, when charging and exposing are repeated great many folds, and have an effectively lowered photomemory property.

This invention is illustrated further with reference to the following examples:

EXAMPLE 1

Copper phthalocyanine of β-type(tradename: Lionol Blue NCB Toner, mfd. by Toyo Ink. Mfg. Co., Ltd.) was purified by heating it successively in water, ethanol, and benzene under reflux, followed by filtration. A mixture of 7 g of the purified pigment, 14 g of a polyester solution(tradename: Polyester Adhesive 49,000, mdf. by Du Pont de Nemours & Co., solid content 20 wt%), 35 g of toluene, and 35 g of dioxane was ground in a ball mill for 6 hours to prepare a dispersion for coating. The dispersion was applied onto an aluminum sheet by means of a Meyer bar and dried to form a charge generation layer 0.5μ thick.

A solution was prepared by dissolving 7 g of the above listed compound H-(1) (2-chloro-4-dimethylaminobenzaldehyde-N-α-naphthyl-N-phnylhydrazone) as a charge-transporting material and 7 g of a polycarbonate (tradename: Panlite K-1300, mfd. by Teijin Kasei Co., Ltd.) in a mixture of 35 g of tetrahydrofuran and 35 g of chlorobenzene with stirring. The solution was applied onto the charge generation layer and dried to form a charge transport layer 11μ thick.

Electrophotographic photosensitive members prepared in this way were corona-charged at −5 KV in the static fashion by using an electrostatic copying paper testing machine (Model SP-428, mfd. by Kawaguchi Denki Co., Ltd.), retained for 10 seconds in the dark, and exposed to light at an intensity of 5 lux to examine their charge bearing characteristics. The results were as follows: where $V_0$ is the surface potential on charging, $V_1$ is the surface potential after 1-second dark decay, and $E_{\frac{1}{2}}$ is the exposure quantity for halving the surface potential $V_1$.

$V_0$: −630 Volt
$V_1$: −620 Volt
$E_{\frac{1}{2}}$: 4.5 lux.sec

Further, a sample of the photosensitive members of this Example was attached around the cylinder of an electrophotographic copying machine to measure variations in light portion potential and dark portion potential when used repeatedly for copying. This copying machine is provided with a ⊖ 5.6-KV corona charging unit, exposure optical unit of exposure quantity 15 lux.sec, development unit, transfer charging unit, exposure optical unit for charge elimination, and cleaner. The machine forms images on a sheet of transfer paper with every revolution of the cylinder. With this copying machine, the light portion potentials ($V_L$) and the dark portion potentials ($V_D$) were measured in the initial copying and after 5000 times of copying. The results were as follows:

Surface potential in the initial copying
$V_D$: −620 Volt
$V_L$: −40 Volt
Surface potential after 5000 times of copying
$V_D$: −610 Volt
$V_L$: −40 Volt

Examples 2–8

Electrophotographic photosensitive members were prepared and tested for electrophotographic characteristics in the same manner as in Example 1 but using the above listed compounds H-(2) through H-(18) as charge-transporting materials in place of the compound H-(1).

The results were as shown in Tables 1 and 2.

TABLE 1

| Example No. | Compound No. | $E_{\frac{1}{2}}$ (lux.sec) | $V_0$ (Volt) | $V_1$ (Volt) |
| --- | --- | --- | --- | --- |
| 2 | H-(2) | 5.2 | −640 | −630 |
| 3 | H-(3) | 7.2 | −600 | −585 |
| 4 | H-(4) | 6.4 | −620 | −615 |
| 5 | H-(5) | 6.7 | −580 | −570 |
| 6 | H-(6) | 6.6 | −605 | −595 |
| 7 | H-(7) | 7.3 | −635 | −620 |
| 8 | H-(8) | 4.4 | −620 | −600 |
| 9 | H-(9) | 4.9 | −600 | −590 |
| 10 | H-(10) | 4.0 | −630 | −620 |
| 11 | H-(11) | 4.3 | −620 | −615 |
| 12 | H-(12) | 3.6 | −610 | −600 |
| 13 | H-(13) | 3.4 | −620 | −605 |
| 14 | H-(14) | 4.2 | −620 | −600 |
| 15 | H-(15) | 4.7 | −640 | −635 |
| 16 | H-(16) | 5.1 | −625 | −615 |
| 17 | H-(17) | 4.9 | −615 | −610 |
| 18 | H-(18) | 4.4 | −605 | −595 |

TABLE 2

| Example No. | Surface potential in the initial copying | | Surface potential after 5000 times of copying | |
| --- | --- | --- | --- | --- |
| | $V_D$ (Volt) | $V_L$ (Volt) | $V_D$ (Volt) | $V_L$ (Volt) |
| 2 | −620 | −40 | −610 | −40 |
| 3 | −580 | −60 | −575 | −60 |
| 4 | −605 | −65 | −595 | −70 |
| 5 | −565 | −40 | −565 | −45 |
| 6 | −585 | −60 | −575 | −60 |
| 7 | −620 | −55 | −615 | −55 |
| 8 | −610 | −35 | −600 | −40 |
| 9 | −580 | −30 | −575 | −30 |
| 10 | −610 | −30 | −610 | −35 |
| 11 | −600 | −30 | −590 | −30 |
| 12 | −590 | −30 | −585 | −30 |
| 13 | −605 | −25 | −600 | −30 |
| 14 | −600 | −35 | −590 | −35 |
| 15 | −620 | −40 | −615 | −40 |
| 16 | −605 | −35 | −600 | −35 |
| 17 | −595 | −30 | −585 | −35 |
| 18 | −585 | −30 | −570 | −30 |

Example 19

A dispersion was prepared by mixing 3 g of 4-(4-dimethylaminophenyl)-2,6-diphenylthiopyrylium perchlorate, 5 g of the above listed hydrazone compound H-(8), 50 g of Polyester Adhesive 49000, and 50 g of a toluene dioxane (50:50) mixture for 6 hours in a ball mill. An aluminum sheet was coated with the dispersion by means of a Meyer bar to a dry thickness of 15μ.

Photosensitive members thus prepared were meausred for electrophotographic characteristics in the same manner as in Example 1. The results were as follows:

$V_0$: −605 Volt
$V_1$: −595 Volt
$E_{\frac{1}{2}}$: 5.2 lux.sec
Surface potential in the initial copying
$V_D$: −585 Volt
$V_L$: −45 Volt
Surface potential after 5000 times of copying
$V_D$: −580 Volt
$V_L$: −45 Volt

Example 20

A solution of casein in an aqueous ammonia (casein 11.2 g, 28% aq. ammonia 1 g, water 222 ml) was applied onto an aluminum sheet by means of a Meyer bar and dried to form an adhesive layer 1μ thick.

A dispersion of 5 g of a disazo pigment having the structure

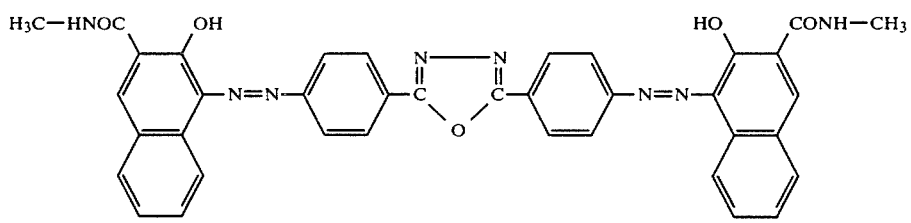

in a solution of 2 g of a vinyl butyral resin (degree of butyral conversion 63 mole %) in 95 ml of ethanol was applied onto the under coating layer and dried to form a charge generation layer 0.4μ thick.

A solution of 5 g of the above listed hydrazone compound H-(12) and 5 g of poly-4,4'-dioxydiphenyl-2,2-propan-carbonate (viscosity average mol. wt. 30,000) in 150 ml of dichloromethane was applied onto the charge generation layer and dried to form a charge transport layer 11μ thick.

Electrophotographic photosensitive members thus prepared were measured for electrophotographic characteristics in the same manner as in Example 1. The results were as follows:
$V_0$: −620 Volt
$V_1$: −615 Volt
$E\frac{1}{2}$: 3.3 lux sec
Surface potential in the initial copying
$V_D$: −610 Volt
$V_L$: −35 Volt
Surface potential after 5000 times of copying
$V_D$: −605 Volt
$V_L$: −35 Volt

Example 21

A molybdenum sheet (substrate) 0.2 mm thick surface-cleaned was fixed on a prescribed position in a glow discharge vapor deposition chamber. The chamber was evacuated to a vacuum of about $5 \times 10^{-6}$ torr. Then, the temperature of the molybdenum substrate was elevated and settled at 150° C. by raising and regulating the input voltage of a heater. Hydrogen gas and silane gas (15 vol. % of hydrogen gas) were introduced into the chamber and the pressure in the chamber was adjusted to 0.5 torr by regulating the gas inflow valves and the main valve of the chamber. Then, 5-MHz high-frequency power was applied to an induction coil to generate a glow discharge in a space inside the chamber surrounded by the coil, and the input power was adjusted to 30 W. Under these conditions, amorphous silicon was deposited on the substrate to a thickness of 2μ. The glow discharge was then stopped, the heater and the high-frequency power source were switched off, the gas inflow valves were closed after the substrate had cooled to 100° C., the chamber was once evacuated to $10^{-5}$ torr, then the chamber pressure was returned to the atmospheric level, and the substrate was taken out. The resulting amorphous silicon layer was then coated with the same charge transport layer in the same manner as in Example 1.

The photosensitive member thus obtained was set in a charging-exposing test apparatus, corona-charged at −6 KV, and immediately thereafter was exposed to a pattern of light which was projected from a tungsten lamp through a transmission type of test chart. A positively charged developer (containing a toner and a carrier) was applied immediately thereafter to the surface of the photosensitive member by the cascade technique. Thus, a good toner image was formed thereupon.

Example 22

After 3 g of 4-(4-dimethylaminophnyl)-2,6-diphenyl-thiopyrylium perchlorate and 3 g of poly(4,4'-isopropylidene-diphenylene-carbonate) were thoroughly dissolved in 200 ml of dichloromethane, a co-crystalline complex was precipitated by adding 100 ml of toluene to the solution. The precipitate was filtered off, and purified by dissolving in dichloromethane, and precipitating again by adding 100 ml of n-hexane.

A dispersion was prepared by mixing 5 g of this co-crystalline complex with 95 ml of methanol containing 2 g of a poly (vinyl butyral) (degree of butyral conversion 63 mol %) in a ball mill for 6 hours. This dispersion was applied by means of a Meyer bar onto a casein layer laid on an aluminum sheet, forming a charge generation of 0.4μ in dry thickness.

Then, the same charge transport layer as prepared in Example 1 were formed on the charge generation layer.

Photosensitive members thus prepared were measured for electrophotographic characteristics in the same manner as in Example 1. The results were as follows:
$V_0$: −600 Volt
$V_1$: −585 Volt
$E\frac{1}{2}$: 5.5 lux.sec
Surface potential in the initial copying
$V_D$: −605 Volt
$V_L$: −45 Volt
Surface potential after 5000 times of copying
$V_D$: −600 volt
$V_L$: −50 Volt

Example 23

A dispersion was prepared by thoroughly mixing 5 g of the same co-crystalline complex as used in Example 22, 5 g of the above listed hydrazone compound H-(13), and 150 ml of tetrahydrofuran containing 100 g of Polyester Adhesive 49,000. This dispersion was applied onto an aluminum sheet by means of a Meyer bar to give a dry coating thickness of 15μ.

Photosensitive members thus prepared were measured for electrophotographic characteristics in the same manner as in Example 1. The results were as follows:
$V_0$: −630 Volt
$V_1$: −615 Volt
$E\frac{1}{2}$: 4.3 lux.sec
Surface potential in the initial copying
$V_D$: −620 Volt
$V_L$: −30 Volt
Surface potential after 5000 times of copying
$V_D$: −610 Volt
$V_L$: −35 Volt

What we claim is:

1. An electrophotographic photosensitive member comprising an electrically conductive substrate and a layer comprising a hydrazone compound represented by the following formula (1) and a binder:

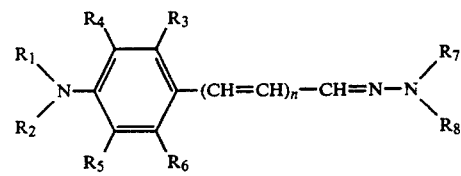

wherein; $R_1$ and $R_2$ each represent alkyl, aralkyl, or aryl, substituted or unsubstituted, or $R_1$ and $R_2$ together with the nitrogen atom to which they are attached form a 5- or 6-membered ring; $R_3$ represents halogen or fluoroalkyl; $R_4$ and $R_6$ each represent hydrogen or halogen; $R_5$ represents hydrogen, alkyl, alkoxy, or halogen; each of $R_7$ and $R_8$ represents alkyl, aralkyl, or aryl, substituted or unsubstituted; and n represents an integer of 0 or 1.

2. The electrophotographic photosensitive member of claim 1, which comprises two photosensitive layers, one being a charge generation layer and the other being a charge transport layer which is said layer containing a hydrazone compound of the formula (1) and a binder.

3. The electrophotographic photosensitive member of claim 2, wherein said charge generation layer comprises at least one photoconductive material selected from the group consisting of selenium, selenium-tellulium, pyrylium series dyes, co-crystalline complexes of pyrylium series dyes, thiopyrylium series dyes, co-crystalline complexes of thiopyrylium series dyes, phthalocyanine series pigments, anthoanthrone pigments, dibenzpyrenequinone pigments, pyranethrone pigments, trisazo pigments, disazo pigments, monoazo pigments, indigo dyes, quinacridone series pigments, asymmetric quinocyanine dyes, quinocyanine dyes, amorphous silicon, squaric acid type dyes, thioindigo series dyes, and perylene series pigments.

4. The electrophotographic photosensitive member of claim 3, wherein said charge generation layer comprises at least one photoconductive material selected from the group consisting of selenium, selenium-tellulium, phthalocyanine series pigments, amorphous silicon, and perylene series pigments.

5. The electrophotographic photosensitive member of claim 4, wherein said charge generation layer is an amorphous silicon film.

6. The electrophotographic photosensitive member of claim 3, wherein said charge generation layer comprises a binder and at least one photocondcutive material selected from the group consisting of pyrylium series dyes, co-crystalline complexes of pyrylium series dyes, thiopyrylium series dyes, co-crystalline complexes of thiopyrylium series dyes, phthalocyanine series pigments, anthoanthrone pigments, dibenzpyrenequinone pigments, pyranethrone pigments, trisazo pigments, disazo pigments, monoazo pigments, indigo dyes, quinacridone series pigments, asymmetric quinocyanine dyes, quinocyanine dyes, squaric acid type dyes, and thioindigo series dyes.

7. The electrophotographic photosensitive member of claim 6, wherein said charge generation layer comprises a phothalocyanine series pigment and a binder.

8. The electrophotographic photosensitive member of claim 7, wherein said phthalocyanine series dye is copper phthalocyanine.

9. The electrophotographic photosensitive member of claim 6, wherein said charge generation layer comprises a disazo pigment and a binder.

10. The electrophotographic photosensitive member of claim 6, wherein said charge generation layer comprises a binder and either a pyrylium series dye or a co-crystalline complex of a pyrylium series dye.

11. The electrophotographic photosensitive member of claim 6, wherein said charge generation layer comprises a binder and either a thiopyrylium series dye or a co-crystalline complex of a thiopyrylium series dye.

12. The electrophotographic photosensitive member of claim 1, wherein said layer comprising a hydrazone compound of the formula (1) and a binder contains further a photoconductive pigment or dye.

13. The electrophotographic photosensitive member of claim 12, wherein said photoconductive pigment or dye is a compound selected from the group consisting of pyrylium series dyes, co-crystalline complexes of pyrylium series dye, thiopyrylium series dyes, co-crystalline complexes of thiopyrylium series dye, phthalocyanine series pigments, anthoanthrone dyes, dibenzpyrenequinone pigments, pyranethrone pigments, trisazo pigments, disazo pigments, monoazo pigments, indigo dyes, quinacridone series pigments, asymmetric quinocyanine dyes, quinocyanine dyes, squaric acid type dyes, and thioindigo series dyes.

14. The electrophotographic photosensitive member of claim 2, wherein said charge transport layer is laid on the upper side of the charge generation layer.

15. The electrophotographic photosensitive member of claim 2, wherein said charge transport layer is laid on the lower side of the charge generation layer.

16. The electrophotographic photosensitive member of claim 1, which has an intermediate layer between the electrically conductive substrate and the layer containing a hydrazone compound of the formula (1) and a binder.

17. The electrophotographic photosensitive member of claim 16, which as the intermediate layer between the electrically conductive substrate and a photosensitive layer comprising a charge generation layer and a charge transport layer which is said layer containing a hydrazone compound of the formula (1) and a binder.

18. The electrophotographic photosensitive member of claim 16, wherein said intermediate layer is an under coating layer.

19. The electrophotographic photosensitive member of claim 1, wherein $R_1$ and $R_2$ in the formula (1) are each methyl, ethyl, propyl, butyl, benzyl, or phenyl.

20. The electrophotographic photosensitive member of claim 1, wherein n in the fomula (1) is zero.

21. The electrophotographic photosensitive member of claim 1, wherein $R_3$ in the formula (1) is chlorine, bromine, iodine or trifluoromethyl.

22. The electrophotographic photosensitive member of claim 1, wherein $R_4$ and $R_6$ are each hydrogen, chlorine, bromine, or iodine.

23. The electrophotographic photosensitice member of claim 1, wherein $R_5$ in the formula (1) is hydrogen, methyl, ethyl, propyl, butyl, methoxy, ethoxy, propoxy, butoxy, fluorine, chlorine, bromine, or iodine.

24. The electrophotographic photosensitive member of claim 1, wherein $R_7$ and $R_8$ in the formula (1) are each methyl, ethyl, propyl, butyl, benzyl, phenethyl, naphthylmethyl, phenyl, naphthyl, or anthryl.

25. The electrophotographic photosensitive member of claim 1, wherein $R_1$ and $R_2$ in the formula (1) together with the nitrogen atom to which they are attached form pyrrolidinyl, piperidino, or morphlino.

* * * * *

UNITED STATES PATENT AND TRADEMARK OFFICE
CERTIFICATE OF CORRECTION

PATENT NO. : 4,487,824

DATED : December 11, 1984

INVENTOR(S) : Kazuharu Katagiri, et al.

It is certified that error appears in the above-identified patent and that said Letters Patent is hereby corrected as shown below:

Title page, under [30] Foreign Application Priority Data

Insert --May 17, 1982 [JP] Japan....81539/1982.--

UNITED STATES PATENT AND TRADEMARK OFFICE
CERTIFICATE OF CORRECTION

PATENT NO. : 4,487,824

DATED : December 11, 1984

INVENTOR(S) : Kazuharu Katagiri et al.

It is certified that error appears in the above-identified patent and that said Letters Patent is hereby corrected as shown below:

Title page, under [56] Foreign Patent Documents.
Insert --
```
        520641              Japan
        157551              Japan
         17105     2/1980   Japan
         94829     8/1976   Japan
       2844394              Japan     --
```

Col. 6, line 5, change "compouding" to --compounding--;
       line 45, change "o-terphenyl" (second occurrence) to
               --p-terphenyl--.

Cols. 9/10, equation (16), change

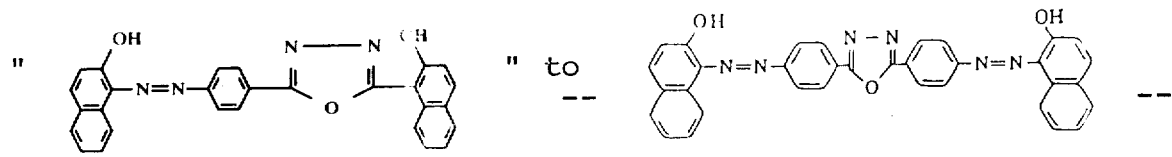

UNITED STATES PATENT AND TRADEMARK OFFICE
CERTIFICATE OF CORRECTION

PATENT NO. : 4,487,824

DATED : December 11, 1984

INVENTOR(S) : Kazuharu Katagiri, et al.

It is certified that error appears in the above-identified patent and that said Letters Patent is hereby corrected as shown below:

Col. 19, line 19, change "Thiodio dyes" to --Thioindio dyes--.

Col. 21, line 21, change "chrolide" to --chloride--;
         line 67, change "naphthol-" to --naphtho- --.

Col. 22, line 20, change "styrenescrylonitrile" to --styreneacrylonitrile--;
         line 46, change "mdf." to --mfd.--;
         lines 54/55, change "phnylhydrazone" to --phenylhydrazone--.

Col. 25, line 58, change "dimethylaminophnyl" to --dimethylaminophenyl--.

Col. 27, line 42, change "phothalocyanine" to --phthalocyanine--.

Col. 28, line 46, change "photosensitice" to --photosensitive--.

Signed and Sealed this

Eighth Day of October 1985

[SEAL]

Attest:

DONALD J. QUIGG

Attesting Officer

Commissioner of Patents and Trademarks—Designate